United States Patent [19]
Kamp et al.

[11] 3,987,661
[45] Oct. 26, 1976

[54] INSTRUMENT FOR TESTING FLAMMABILITY

[75] Inventors: Arnold Cornelis Francois Kamp; Richard Stephen Lewis, both of Mitcham, England

[73] Assignee: Oertling Limited, Orpington, United Kingdom

[22] Filed: Sept. 3, 1975

[21] Appl. No.: 610,006

[30] Foreign Application Priority Data
Sept. 6, 1974 United Kingdom............... 39103/74

[52] U.S. Cl............................................... 73/15 R
[51] Int. Cl.²........................................ G01N 25/00
[58] Field of Search........................ 73/15 R, 15.4

[56] References Cited
UNITED STATES PATENTS

| | | | |
|---|---|---|---|
| 3,545,252 | 12/1970 | Springfield et al. | 73/15 |
| 3,578,756 | 5/1971 | Evans et al. | 73/15 |
| 3,593,563 | 7/1971 | Marmor et al. | 73/15.4 |
| 3,662,586 | 5/1972 | Suga | 73/15 |
| 3,820,379 | 6/1974 | Nelson et al. | 73/15 |

FOREIGN PATENTS OR APPLICATIONS
161,560  7/1964  U.S.S.R................................. 73/15

OTHER PUBLICATIONS
"Fire Test Adopted as Standard" in Scientific America 5/34 pp. 268 and 272.

*Primary Examiner*—Herbert Goldstein
*Attorney, Agent, or Firm*—Wenderoth, Lind & Ponack

[57] ABSTRACT

The instrument tests specimens by means of the critical oxygen index method and comprises a twin-walled chimney of transparent material in which the specimen is mounted. A helically wound heater coil is positioned between the chimney walls to heat the interior of the chimney and a preheater is provided to enable gases entering the chimney to be heated, the combination of heaters enabling a closely controlled temperature gradient to be maintained around the specimen. The specimen is tested by introducing into the chimney a variable mixture of nitrogen and oxygen and igniting the specimen under controlled conditions.

14 Claims, 7 Drawing Figures

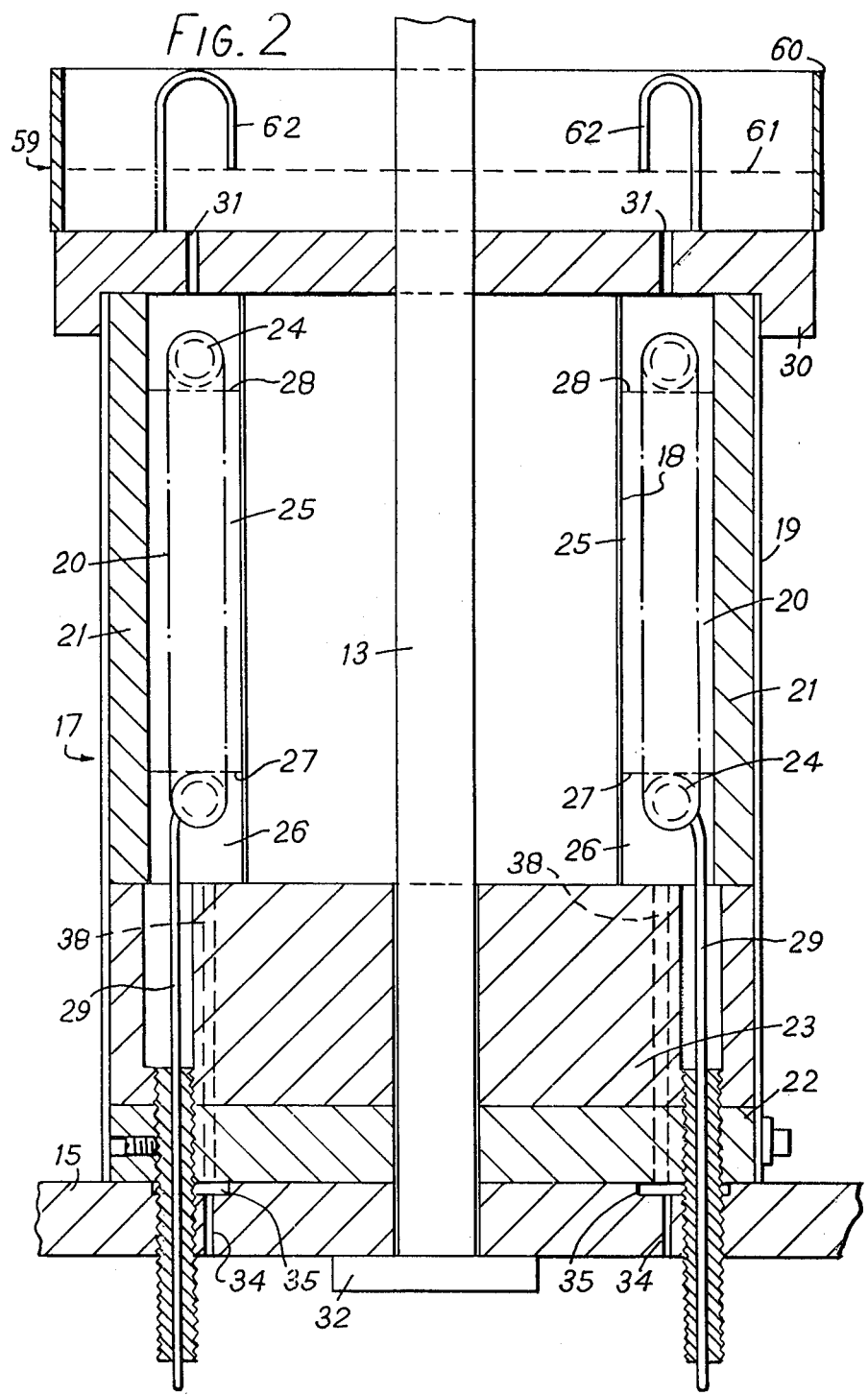

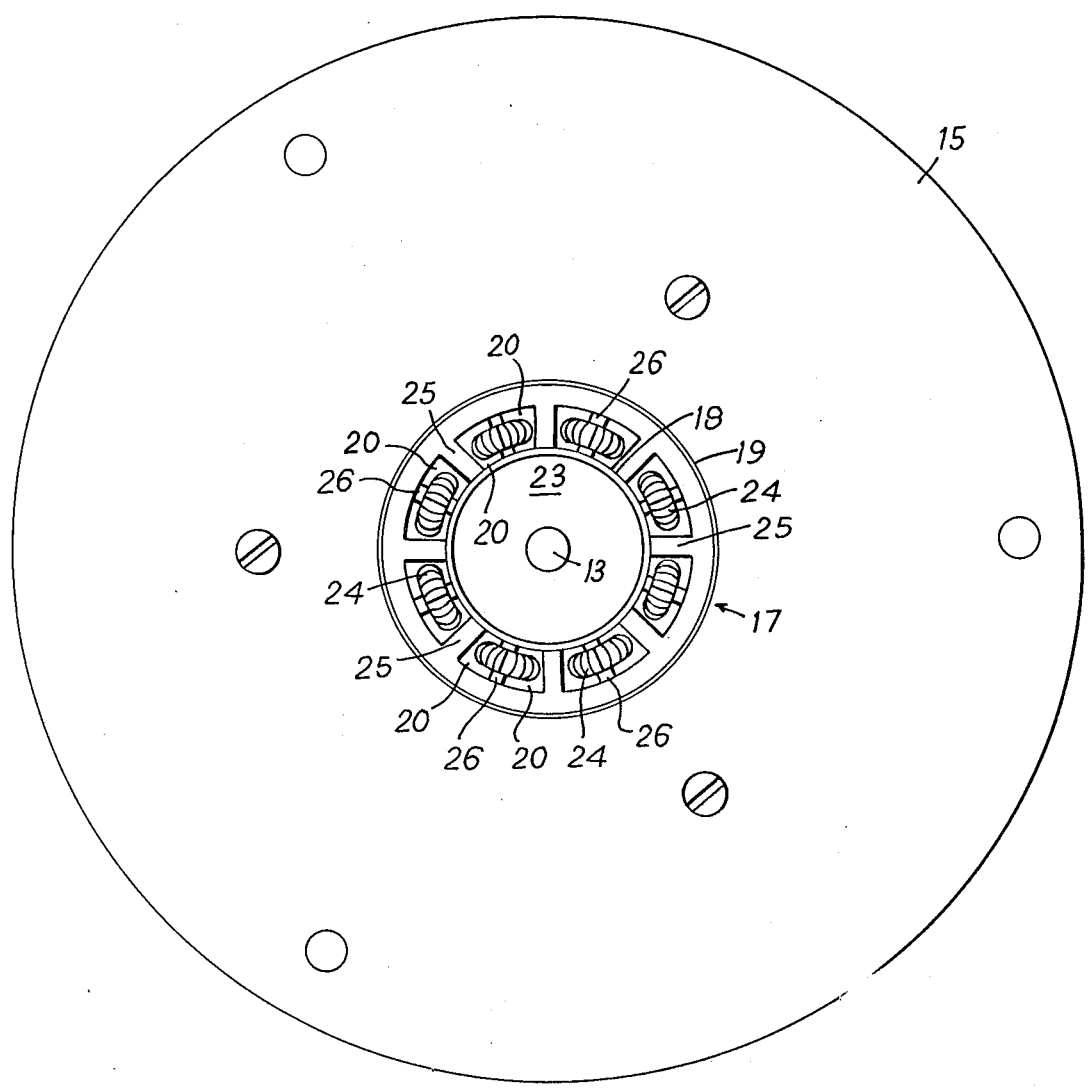

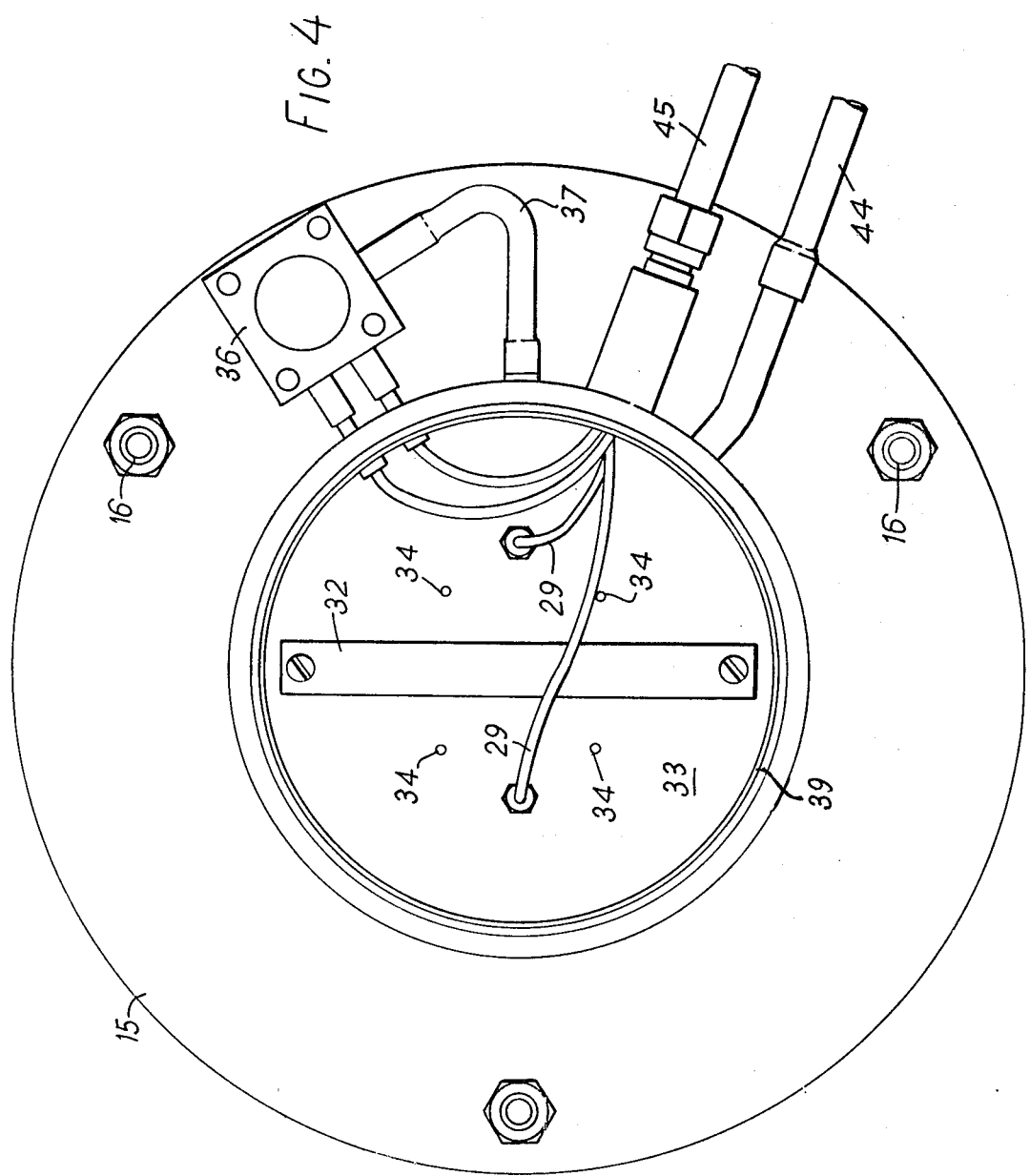

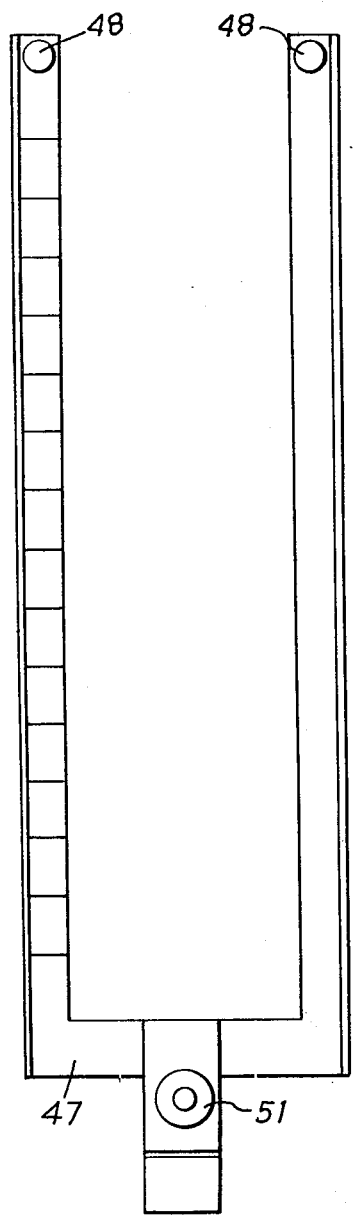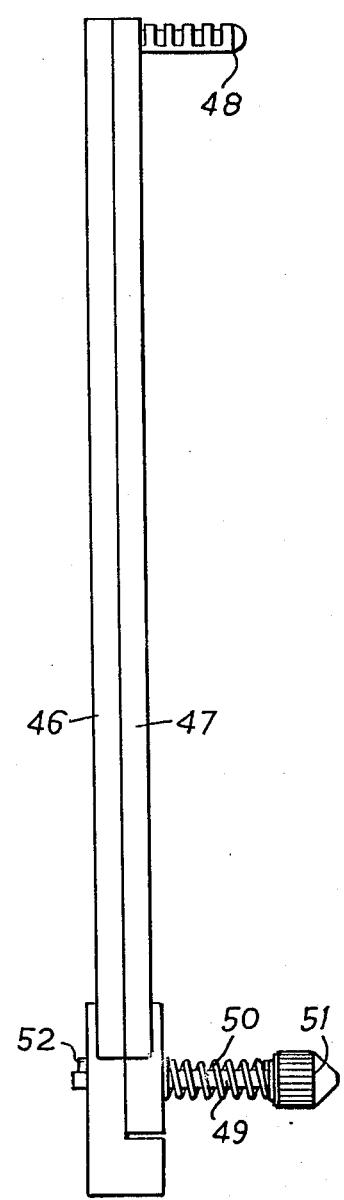

INSTRUMENT FOR TESTING FLAMMABILITY

This invention relates to instruments for testing flammability by the critical oxygen index (C.O.I.) method. In such instruments, an elongated specimen is supported in a vertical chimney, the lower end of which is supplied with a controlled mixture of oxygen and nitrogen at a controlled rate. The upper end of the specimen is ignited by the application of a flame under controlled conditions, and by varying the proportion of oxygen, it is possible to establish the minimum proportion of oxygen at which combustion of the specimen can be maintained.

It is important to be able to carry out such tests at elevated temperatures since with many materials the C.O.I. values fall, in some cases dramatically, with increasing temperatures. It has therefore been proposed to heat the gases supplied to the chimney and, also, to heat the chimney itself either by winding round it a heating tape or by forming it from a furnace tube which has an embedded heating element. In either case it is desirable to lag the chimney in order to reduce heat losses.

Such arrangements are not satisfactory; since on the one hand it is very difficult to observe the ignition or the subsequent combustion, and on the other hand it is difficult to arrange a uniform distribution of temperature along the length of the specimen.

According to the invention, there is provided an apparatus for testing the flammability of a specimen, said apparatus comprising a vertical chimney composed of two transparent tubular members, one arranged coaxially within and spaced from the other, a specimen support situated within the inner one of said tubular members, an electric heating element arranged in the space between the tubular members, and means for supplying a mixture of oxygen and nitrogen to one end of the chimney.

Preferably the heating element, which may be formed of nickel chromium or other resistance wire, is wound round the inner member and the spacing of the turns of the winding may decrease towards the upper end to provide a graded heating effect. The tubular members may be circular or rectangular in section or any other shape required to produce uniform transverse radiant heating of the specimen.

The use of a two walled chimney considerably reduces heat losses from the interior and enables desired temperature conditions within the chimney to be maintained. Furthermore, the exterior surface of the outer tubular member is relatively cool, thus reducing the likelihood of injury to operators.

For use up to temperatures of the order of 500° C the tubular members may be made of a heat resistant glass such as Pyrex. For temperatures up to about 1000° C quartz may be used at least for the inner member, and it is practicable to use this material up to temperatures of 1300° C if it is prevented from devitrifying by ensuring that it is never cooled below 300° C.

An electric preheater may, also, be provided for heating the gas mixtures supplied to the chimney, and this preheater and the heater in the chimney may be provided with a suitable control so as to ensure that in use the temperature of the specimen is held constant along its length. Suitably arranged thermo-couples may be provided in order to monitor the temperature, and it is contemplated that automatic equipment be provided for maintaining the temperature at the desired value.

In order that the invention may be better understood, an embodiment thereof will now be described by way of example only and with reference to the accompanying drawings in which:

FIG. 2 is a cross sectional elevation of the preheater used in the apparatus of FIG. 1;

FIG. 3 is a plan view of the preheater of FIG. 2, with the top plate and tray assembly removed;

FIG. 4 is a view looking upwards of the lower part of the apparatus, with the base portion removed;

FIGS. 5 and 6 are side views of a different type of specimen holder for use in the apparatus of FIG. 1.

Figure 1:
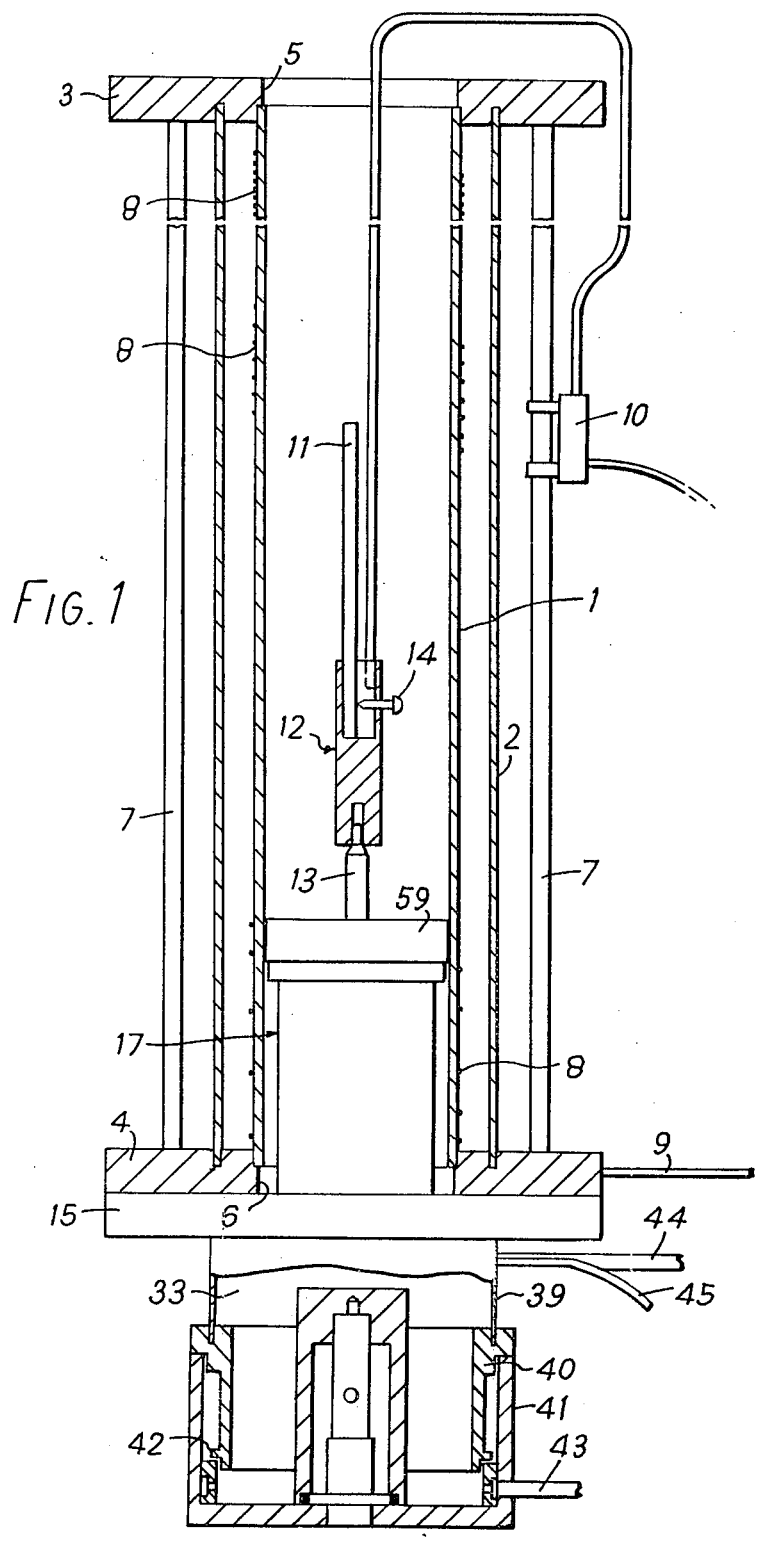
FIG. 1 is a cross sectional elevation of an embodiment of a flammability testing apparatus according to this invention.

Referring to the drawings, the apparatus comprises a pair of transparent tubular members 1,2 held and located by end plates 3,4. The end plates are made from pressure formed asbestos board such as natural syndanyo. The transparent members, 1,2 are made of pyrex, although higher temperatures may dictate the use of high temperature materials such as quartz. The end plates are each formed with a suitably disposed groove in which the outer member 2 is located. The inner member 1 is located by an enlarged portion of a circular aperture 5 in the plate 3 and a circular aperture 6 in the plate 4. The assembly is held together by a plurality of tie rods 7, two of which are shown in FIG. 1. An electric heating element in the form of a helically wound coil 8 is arranged within the space between the tubular members 1,2. For the purpose of clarity, only certain of the windings of the coil 8 are illustrated. The spacing between the turns of coil 8 is graded so as to be narrower at the top than at the bottom. Furthermore, the ratio of the diameter of the wire making up the heating coil to the spacing between the turns is such as not to interfere with proper observation of a specimen within the member 1. A lead 9 supplies electrical power to the heating coil 8.

The vertical temperature distribution within the member 1 may be monitored by means of a thermo-couple 10 which is slideable on one of the tie bars 7 and is also moveable radially within the member.

A specimen 11 to be tested is mounted in a specimen holder 12 which is itself mounted on the narrowed upper end of a spigot assembly 13. The specimen holder 12 comprises a metal rod which is axially apertured at each end to receive, in one case, the specimen and, in the other case, the upper end of the assembly 13. A bolt 14 is threaded into the wall of the upper aperture to secure the specimen. It will be noted that the specimen holder described above is suitable for mounting only rigid specimens. A holder suitable for non-rigid specimens is to be described hereafter.

The lower end plate 4 is bolted to a base plate 15, also of pressure formed asbestos board, by means of three nut and bolt assemblies 16. The nut-and-bolt assemblies 16 are omitted in FIG. 1 for clarity. The base plate 15 mounts a preheater 17 which is shown in detail in FIGS. 2 and 3. The preheater comprises a circular inner wall 18 and outer wall 19, both of high temperature alloy, the space between which is divided to provide a plurality of axially extending chambers 20 by means of a block 21 of ceramic material. The lower part of the preheater includes a disc 22 of pressure formed asbestos board on top of which is positioned a block 23 of firebrick. The area above the block 23 between the walls 18 and 19 contains a coiled heating element 24, typically of 100 to 400 watts power, which extends in zig-zag fashion from chamber to chamber.

Each chamber 20 has a width defined by a pair of side walls 25, 26 formed from the block 21. The side walls 25 each extend downwards from the top of the walls 18 and 19 to a level indicated by the line 27 in FIG. 2. Similarly, the side walls 26 extend upwards from the upper surface of block 23 to a level indicated by line 28 in FIG. 2. The element 24 is thus able to extend continuously from chamber to chamber, although in practice the element is split in half, the two halves being connected in series across the supply. Electrical power for the preheater element 24 is supplied through a pair of supply leads 29 which pass downwards through the block 23, disc 22 and base plate 15 and are sealed to ensure a gas tight connection between the chambers 20 and the underside of the base plate 15.

The upper end of the preheater is covered by a diffuser plate 30 of firebrick in which is formed a plurality of small apertures 31 communicating with the chambers 20. These apertures form output apertures for the gas mixture which flows through the chambers 20. The tortuous path which the gas has to follow ensures good mixing of the gases. The plates 15 and 30, disc 22 and block 23 are each formed with a coaxial central aperture through which extends the spigot assembly 13. The spigot assembly comprises a central spigot on the upper end of which is mounted the specimen holder and an elongated mounting plate 32 which is bolted to the base plate 15.

The gas mixture enters the chambers 20 from a mixing chamber 33 (see FIG. 1) beneath the plate 15. The mixed gas first passes through the plate 15 via four small passages 34 into an annular groove 35 formed in the upper surface of plate 15. The diameter of the passages 34 is such as to maintain a small pressure within the chamber 33 which can be monitored by means of a pressure sensor 36. The pressure sensor communicates with chamber 33 through a tube 37 and acts to cut off the supply of current to the heating coil 8 and heater element 24 if a gas leak should develop in that part of the gas flow system prior to entering the chambers 20. If desired, the pressure sensor may also activate an alarm to give warning of a fault.

From the annular groove 35, the mixed gas passes through eight passages 38 through the disc 22 and block 23 into the bottom of the chambers 20. Each of the eight passages 38 opens into the chambers 20 at a position directly beneath a respective wall 25, so that the gas mixture from each passage 38 divides evenly between two adjacent chambers.

The chamber 33 is defined by an upper wall 39 of stainless steel which fits in a cylindrical portion 40 of aluminium. The portion 40 is sized to fit into a standard base 41 and the chamber is sealed by means of an O-ring 42. In the particular embodiment illustrated, the apparatus rests on the base by gravity, although separate fixing means can, of course, be used if required. Any loss of pressure at the O-ring will immediately be detected by the sensor 36 and the heating elements will be cut off to prevent damage. The already mixed gas enters chamber 33 through a pipe 43 in the base 41. A further pipe 44 supplies air to the chamber 33, for a purpose to be described hereafter. The electrical connections to the element 24 and to the pressure sensor 36 are taken away in a four core lead 45 which is sealingly connected to the upper wall 39 of the chamber 33.

An alternative specimen holder for mounting non-rigid specimens is shown in detail in FIGS. 5 and 6. The holder comprises a pair of fork-shaped metal elements 46,47 between which a specimen (not shown) is clamped. The element 46 is equipped, at the remote end of each tooth, with an upstanding notched projection 48. The element 47 is equipped with corresponding apertures so that the two elements can take up a number of discrete selected positions spaced apart from one another. By this means the two elements are effectively pivoted with respect to one another and clamping is effected by a spring loaded mechanism. This mechanism comprises a rod 49 around which is supported a coil spring 50. The spring 50 acts between the element 47 and a knob 51 to tend to bias the rod 49 in a direction towards the right in FIG. 6. Movement of the rod in this direction is limited by a small peg 52 affixed to rod 49, which peg is biassed against the element 46 by virtue of the spring 50, thus clamping the elements 46,47 and any specimen positioned between them, together. Various thicknesses of specimen can be accommodated by employing different notches on the projections 48.

Figure 7:
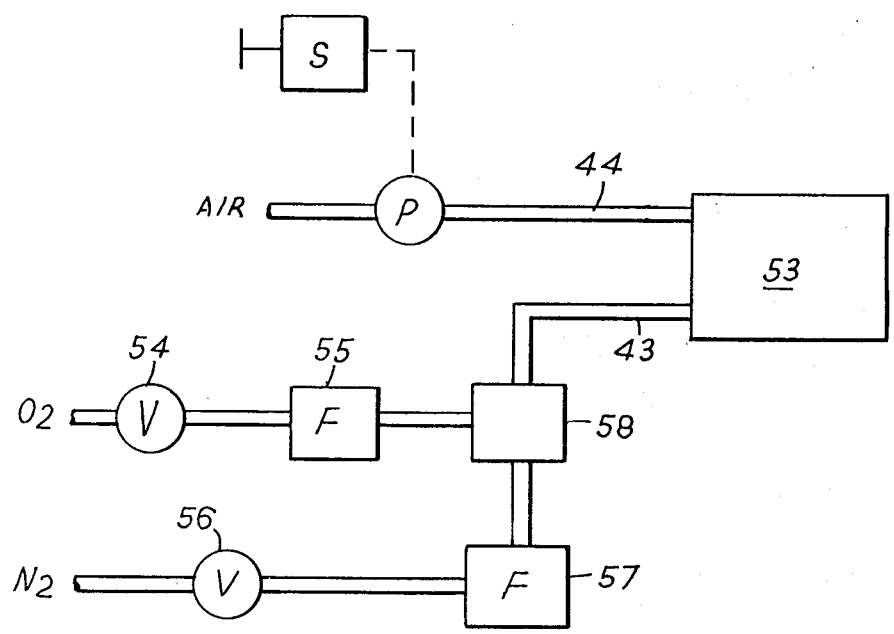
FIG. 7 is a block diagram illustrating the arrangement for supplying gas to the apparatus.

FIG. 7 shows diagramatically how the apparatus described above, shown under reference 53, can be connected to a gas supply system. As mentioned previously, for normal testing, a controlled mixture of oxygen ($O_2$) and nitrogen ($N_2$) is passed up the vertical chimney and combustion of the specimen is examined under varying conditions. The oxygen supply is taken from a gas source, through a variable flow valve 54 and filter 55. Similarly, the nitrogen supply is taken from a gas source through a variable flow valve 56 and filter 57. The outputs of the filters 55 and 57 are combined in a mixing filter 58 where a thorough mixing of the gases takes place. The output from the filter 58 is taken via line 43 to the mixing chamber 33 (see FIG. 1). The proportion of oxygen and nitrogen in the mixed gas entering the chamber 33 may be varied by means of the valves 54 and 56 which are under the control of the operator.

Each time a test is carried out, it is first necessary to stabilise the temperature conditions within the chimney so that the conditions under which the test is carried out are accurately determined. It may, for example, be wished to examine combustion of the specimen under particular temperature conditions, for example, with a particular temperature gradient present along the specimen. For this purpose it is necessary to run the apparatus for some time prior to actual ignition of the specimen to enable the required conditions to establish themselves. This is achieved in the above described apparatus by passing air, rather than the oxygen/nitrogen mixture, through the apparatus while the preheater and chimney heater are switched on to establish the required conditions. The air is pressurized by means of a pump P and is supplied to the chamber 33 through the pipe 44. The pump is controlled by a push button switch S. When the apparatus has reached the required temperature, and conditions have stabilised, the oxygen/nitrogen mixture is introduced into chamber 33 and the pump p is switched off to inhibit the supply of air. The switch-over from air to oxygen/nitrogen mixture is such that the pressure in chamber 33 is maintained, so the apparatus is not shut down, even briefly, during the change. From the above description, it is seen that the arrangement of this invention allows the apparatus to be accurately set up for particular conditions without wastage of oxygen and nitrogen.

When the required conditions have been established, and the oxygen/nitrogen mixture is flowing up the chimney, the upper part of the specimen is ignited and combustion is observed through the transparent walls of the chimney. Ash and other particles falling off the specimen during combustion are collected on a wire mesh tray assembly 59 shown in detail in FIG. 2. The assembly 59 comprises a cylindrical metal side wall 60 and a circular wire mesh tray 61 attached thereto along its perimeter. Three equiangularly spaced hooks 62 are attached to the wire mesh to enable the assembly 59 to be hooked out from the top of the chimney for cleaning. In normal useage, the tray assembly merely rests directly on top of the diffuser plate 30.

The use, in the above described apparatus, of a preheater in combination with a chimney heater enables the high temperature conditions present in a real fire to be much more readily duplicated. Further, the use of two separate heaters, both individually controlled, enables very precise temperature conditions along the specimen to be set up. In particular, even temperature conditions along the specimen may easily be attained. By varying the proportion of preheater power to chimney heater power, accurate temperature gradients can be set up. Furthermore, the possibility of automatic closed loop control, using the thermocouple 10 to control the outputs of the two heaters is a possibility. The thermocouple may be connected to a digital temperature readout to facilitate temperature gradient observations.

We claim:

1. An apparatus for testing the flammability of a specimen comprising:
    a vertical chimney comprised of inner and outer transparent concentric tubular members arranged one within the other and spaced from each other;
    specimen support means positioned within the inner tubular member for supporting said specimen;
    electric heating means arranged in the space between said tubular members for graded heating of said inner tubular member, said heating means comprised of:
    a helically wound coil wound about the inner tubular member in the space between the inner and outer tubular members, said coiled wire having the spacings between the coil loops decreasing in width toward the top of said inner tubular member, whereby a graded heating effect is achieved;
    oxygen and nitrogen supply means operatively connected to the inside of said inner tubular member for supplying oxygen and nitrogen thereinto; and
    mixing chamber means connected between said oxygen and nitrogen supply means and said inner tubular member for receiving the oxygen and nitrogen before it passes to the inner tubular member.

2. An apparatus as claimed in claim 1 wherein said helically wound coil is comprised of a wire of sufficiently thin diameter in comparison to the distance between the windings of the coil to permit observation of the specimen within said inner tubular member.

3. An apparatus as claimed in claim 1 further comprising preheating means between said mixing chamber means and the inner tubular member for heating gases supplied to said inner tubular member.

4. An apparatus as claimed in claim 3 wherein said preheating means is comprised of:
    a plurality of parallel elongated chambers above said mixing chamber means;
    heating element means positioned in each of said chambers for heating said chambers; and
    gas supply means connected to said chambers and said mixing chamber means for supplying gas to each of said chambers from said mixing chamber means.

5. An apparatus as claimed in claim 4 wherein said heating element means is comprised of at least one heating coil passing continuously through said parallel elongated chambers.

6. An apparatus as claimed in claim 1 further comprising tray assembly means beneath said specimen support means for catching ash and debris falling downward in said inner tubular member.

7. An apparatus as claimed in claim 1 further comprising air supply means connected to mixing chamber means for selectively supplying pressurized air into said mixing chamber means.

8. An apparatus as claimed in claim 1 further comprising pressure sensor means connected to said mixing chamber means for monitoring the pressure of the gas in said mixing chamber means.

9. An apparatus as claimed in claim 8 wherein said pressure sensing means is operatively connected to said heating means for disconnecting the current to said heating means when the pressure in said mixing chamber means falls below a predetermined value.

10. An apparatus as claimed in claim 8 further comprising an alarm means connected to said pressure sensing means for signaling when the pressure in said mixing chamber means falls below a predetermined value.

11. An apparatus as claimed in claim 1 further comprising temperature monitoring means in said inner tubular member for monitoring the temperature therein.

12. An apparatus as claimed in claim 11 wherein said temperature monitoring means is movable axially and radially within said inner tubular member, whereby a temperature gradient along the specimen in said inner tubular member can be determined.

13. An apparatus as claimed in claim 11 wherein said temperature monitoring means is a thermocouple.

14. An apparatus as claimed in claim 11 wherein said temperature monitoring means is operatively connected to said heating means for automatically controlling the electric current to said heating means.

* * * * *